(12) United States Patent
Maczura et al.

(10) Patent No.: US 6,836,325 B2
(45) Date of Patent: Dec. 28, 2004

(54) OPTICAL PROBES AND METHODS FOR SPECTRAL ANALYSIS

(75) Inventors: Anthony K. Maczura, Reading, MA (US); Erich R. Gross, Rohnert Park, CA (US); Anthony S. Lee, Petaluma, CA (US); David M. Mayes, LaGrande, OR (US)

(73) Assignee: Textron Systems Corporation, Wilmington, MA (US)

(*) Notice: Subject to any disclaimer, the term of this patent is extended or adjusted under 35 U.S.C. 154(b) by 376 days.

(21) Appl. No.: 09/932,210

(22) Filed: Aug. 17, 2001

(65) Prior Publication Data

US 2001/0055116 A1 Dec. 27, 2001

Related U.S. Application Data

(63) Continuation-in-part of application No. 09/803,131, filed on Mar. 9, 2001, now Pat. No. 6,753,966, and a continuation-in-part of application No. 09/354,497, filed on Jul. 16, 1999, now abandoned, and a continuation-in-part of application No. 09/426,826, filed on Oct. 25, 1999, now Pat. No. 6,424,416.

(51) Int. Cl.$^7$ .................................................. G01J 3/42
(52) U.S. Cl. ...................................... 356/328; 356/445
(58) Field of Search .............................. 356/326, 328, 356/419; 250/339.07, 339.11, 339.12, 341.8

(56) References Cited

U.S. PATENT DOCUMENTS

| | | | |
|---|---|---|---|
| 3,281,597 A | 10/1966 | Greenberg | 250/43.5 |
| 3,773,424 A | 11/1973 | Selgin | 356/181 |
| 4,003,660 A | 1/1977 | Christie, Jr. et al. | 356/178 |
| 4,260,262 A | 4/1981 | Webster | 356/418 |
| 4,260,263 A | 4/1981 | Kummer | 356/448 |
| 4,266,878 A | 5/1981 | Auer | 356/419 |

(List continued on next page.)

FOREIGN PATENT DOCUMENTS

| | | |
|---|---|---|
| DE | 2938844 | 4/1981 |
| DE | 3401475 A1 | 7/1985 |
| EP | 0 491 131 A1 | 6/1992 |
| EP | 0 806 653 | 5/1997 |
| EP | 0 806 653 B1 | 5/2001 |
| GB | 2 084 723 A | 4/1982 |
| JP | 11-83627 | 7/1989 |
| JP | 6138043 | 5/1994 |
| JP | 11-83627 A | 3/1999 |
| WO | WO 96/08710 | 3/1996 |
| WO | WO 98/11410 | 3/1998 |
| WO | WO 99/40419 | 8/1999 |

OTHER PUBLICATIONS

Baird et al.; "Compact, Self–Contained Optical Spectrometer", Appl. Spec. v.49 (11): 1, (1997).

Department of Biosystems and Agricultural Engineering, University of Minesota, 1995 Annual Report Research.

Ciurczak; Emil W. "Uses of Near–Infrared Spectroscopy in Pharmaceutical Analysis", Applied Spectroscopy Reviews 23(1 & 2), 147–163 (1987).

(List continued on next page.)

Primary Examiner—F. L. Evans
(74) Attorney, Agent, or Firm—Foley Hoag, LLP

(57) ABSTRACT

The present invention relates to spectral analysis systems and methods for determining physical and chemical properties of a sample by measuring the optical characteristics of light emitted from the sample. In one embodiment, a probe head for use with a spectrometer includes an optical blocking element for forcing the optical path between the light source and an optical pick-up optically connected to the spectrometer into the sample. The probe head also includes a reference shutter for selectively blocking light emitted from the sample from reaching the optical pick-up to facilitate calibration of the spectrometer.

36 Claims, 5 Drawing Sheets

U.S. PATENT DOCUMENTS

| | | |
|---|---|---|
| 4,286,327 A | 8/1981 | Rosenthal et al. .......... 364/498 |
| 4,403,191 A | 9/1983 | Satake ........................ 324/452 |
| 4,441,979 A | 4/1984 | Dailey ........................ 204/402 |
| 4,540,286 A | 9/1985 | Satake et al. ............... 356/445 |
| 4,627,008 A | 12/1986 | Rosenthal ................... 364/550 |
| 4,658,147 A | 4/1987 | Eldering |
| 4,692,620 A | 9/1987 | Rosenthal ................... 250/343 |
| 4,729,247 A | 3/1988 | Brown |
| 4,752,689 A | 6/1988 | Satake ........................ 250/339 |
| 4,806,764 A | 2/1989 | Satake ........................ 250/339 |
| 4,968,143 A | 11/1990 | Weston |
| 4,997,280 A | 3/1991 | Norris ........................ 356/308 |
| 5,013,150 A | 5/1991 | Watts et al. |
| 5,021,662 A | 6/1991 | Johnson ...................... 250/343 |
| 5,077,481 A | 12/1991 | Hoult |
| 5,092,819 A | 3/1992 | Schroeder et al. ............. 460/7 |
| 5,106,339 A | 4/1992 | Braun et al. .................... 460/7 |
| 5,128,882 A | 7/1992 | Cooper et al. .............. 364/550 |
| 5,148,288 A | 9/1992 | Hannah ...................... 358/298 |
| 5,155,628 A | 10/1992 | Dosmann .................... 359/640 |
| 5,159,199 A | 10/1992 | LaBaw ........................ 250/339 |
| 5,166,755 A | 11/1992 | Gat ............................. 356/419 |
| 5,179,025 A | 1/1993 | Koontz et al. ................ 436/52 |
| 5,205,293 A | 4/1993 | Ito et al. ...................... 128/691 |
| 5,206,699 A | 4/1993 | Stewart et al. ................ 356/30 |
| 5,218,207 A | 6/1993 | Rosenthal ................... 250/341 |
| 5,241,178 A | 8/1993 | Shields ........................ 250/339 |
| 5,258,825 A | 11/1993 | Reed et al. ................. 356/402 |
| 5,260,584 A | 11/1993 | Popson et al. .............. 250/571 |
| 5,272,518 A | 12/1993 | Vincent ...................... 356/405 |
| 5,319,200 A | 6/1994 | Rosenthal et al. .......... 250/341 |
| 5,327,708 A | 7/1994 | Gerrish ............................ 56/1 |
| 5,335,067 A | 8/1994 | Prather et al. |
| 5,351,117 A | 9/1994 | Stewart et al. ................ 356/30 |
| 5,377,000 A | 12/1994 | Berends ........................ 356/73 |
| 5,383,452 A | 1/1995 | Buchert ...................... 128/633 |
| 5,406,084 A | 4/1995 | Tobler et al. .......... 250/339.01 |
| 5,418,615 A | 5/1995 | Doyle |
| 5,433,197 A | 7/1995 | Stark .......................... 128/633 |
| 5,459,313 A | 10/1995 | Schrader et al. ........ 250/223 B |
| 5,460,177 A | 10/1995 | Purdy et al. ................ 128/633 |
| 5,461,229 A | 10/1995 | Sauter et al. ............... 250/253 |
| 5,464,981 A | 11/1995 | Squyres et al. .......... 250/341.8 |
| 5,475,201 A | 12/1995 | Pike ............................ 219/497 |
| 5,476,108 A | 12/1995 | Dominguez et al. ........ 131/108 |
| 5,480,354 A | 1/1996 | Sadjadi ............................ 460/7 |
| 5,489,980 A | 2/1996 | Anthony ...................... 356/308 |
| 5,502,799 A | 3/1996 | Tsuji et al. .................. 395/131 |
| 5,503,006 A | 4/1996 | Babaian-Kibala et al. ..... 73/86 |
| 5,510,619 A | 4/1996 | Zachmann et al. .... 250/339.08 |
| 5,548,115 A | 8/1996 | Ballard et al. ............... 250/253 |
| 5,616,851 A | 4/1997 | McMahon et al. ......... 73/29.01 |
| 5,625,459 A | 4/1997 | Driver ........................ 356/446 |
| 5,642,498 A | 6/1997 | Kutner ........................ 395/509 |
| 5,652,810 A | 7/1997 | Tipton et al. |
| 5,654,496 A | 8/1997 | Thompson .................. 73/1.01 |
| 5,676,143 A | 10/1997 | Simonsen et al. .......... 128/633 |
| 5,684,582 A | 11/1997 | Eastman et al. ............. 356/328 |
| 5,736,410 A | 4/1998 | Zarling et al. ............... 436/172 |
| 5,739,536 A | 4/1998 | Bucholtz et al. .......... 250/341.2 |
| 5,745,234 A | 4/1998 | Snail et al. .................. 356/236 |
| 5,751,421 A | 5/1998 | Wright et al. ............... 356/328 |
| 5,784,158 A | 7/1998 | Stanco et al. ............... 356/326 |
| 5,808,305 A | 9/1998 | Leidecker et al. ....... 250/341.8 |
| 5,813,987 A | 9/1998 | Modell et al. ............... 600/473 |
| 5,824,567 A | 10/1998 | Shih et al. .................... 438/73 |
| 5,847,825 A | 12/1998 | Alexander .................. 356/318 |
| 5,867,265 A | 2/1999 | Thomas ...................... 356/328 |
| 5,872,655 A | 2/1999 | Seddon et al. .............. 359/588 |
| 5,880,826 A | 3/1999 | Jung et al. .................... 326/73 |
| 5,884,775 A | 3/1999 | Campbell .................... 209/581 |
| 5,953,119 A | 9/1999 | Zigler et al. ................. 356/326 |
| 5,957,773 A | 9/1999 | Olmsted et al. ................ 460/7 |
| 6,100,526 A | 8/2000 | Mayes ................... 250/339.11 |
| 6,424,416 B1 | 7/2002 | Gross et al. |

OTHER PUBLICATIONS

Geladi et al.; "Linearization and Scatter–Correction for Near–Infrared Reflectance Spectra of Meat", Applied Spectroscopy, 39(3): 491–500, (1985).

Goddu et al.; "Spectra–Structure Correlations for the Near–Infrared Region", Analytical Chemistry, 32(1): 140–142, (Jan. 1960).

Honigs et al.; "Near–Infrared Reflectance Analysis by Gauss–Jordan Linear Algebra", Applied Spectroscopy, 37(6): 491–497, (1983).

Honigs et al.; "A New Method for Obtaining Individual Component Spectra from Those of Complex Mixtures", Applied Spectroscopy, 38(3): 317–322, (1984).

Josefson et al.; "Optical Fiber Spectrometry in Turbid Solutions by Multivariate Calibration Applied to Tablet Dissolution Testing", Anal. Chem. 60: 2666–2671, (1988).

Keefe P. D.; "A Dedicated Wheat Grain Image Analyser", Plant Varieties and Seeds, 5:27–33, (1992).

Kisner and Brown, "Multiple Analytical Frequencies and Standard for the Least–Squares Spectrometric Analysis of Serum Lipids", Anal. Chem. 55:1703–1707, (1983).

Lutton Christine.; "Cyberfarm", Forbes, Jul. 15, 1996.

Mosen et al.; "Determination of Impurities in Helium by Gas Chromatography", Analytical Chemistry, 32(1): 141–142, (1960).

Nyden et al.; "Spectroscopic Quantitative Analysis of Strongly Interacting Systems: Human Plasma Protein Mixtures", Applied Spectroscopy ,42 (4): 588–594, (1988).

Norris et al.; "Predicting Forage Quality Infrared Reflectance Spectroscopy", Journal of the Animal Science 43 (4): 889–897, (1976).

Osborne and Fearn; "Discriminant Analysis of Black Tea by Near Infrared Reflectance Spectroscopy", Food Chemistry 29 (1): 233–238, (1988).

Schneider et al.; "Fiber–Optic Near Infrared Reflectance Sensor For Detection of Organics in Soils", IEEE Photonics Technology Letters 7(1): 87–89, (1995).

Stark and Luchter; "Near Infrared Analysis (NIRA): A Technology for Quantitative and Qualitative Analysis", Applied Spectroscopy Reviews 22(4): 335–399, (1986).

Starr et al.; "Application of Near Infrared Reflectance Analysis in Breeding Wheats for Bread–making Quality", Near Infrared Analysis– Today and Tomorrow?, Anal. Proc., 20: 72–74, (Feb. 1983).

Watson, C. A. ; "Near Infrared Reflectance Spectrophotometric Analysis of Agricultural Products", Analytical Chemistry 49(9): 835A–839, (Aug. 1977).

Wetzel L. David; "Near –Infrared Reflectance Analysis: Sleeper Among Spectroscopic Techniques", Analytical Chemistry 55(12): 1165A–1175A, (Oct. 1983).

Winch and Major; "Predicting Nitrogen and Digestibility of Forage Using Near Infrared Reflectance Photometry", Can. J. Plant Sci. 61:45–51, (Jan. 1981).

Better Crops With Plant Food(Journal), vol. 81 No. 4, (1997).

Yamamoto et al.; "Detection of Metals in the Environment Using a Portable Laser–Induced Breakdown Spectroscopy Instrument", Appl. Spec. V. 50(2) Abstract Only, (1997).

Rhea Corporation; "Suppliers of Krestrel™ brand Systems for Imaging Spectroscopy", Rhea Corporation Information Sheet Sep. 22, 1997.

Perstorp Analytical Information Sheet, www.i–way.net.uk/sinar/product.

Fundamentals Near Infrared Instrumentation, Infrared Detectors information sheet.

Derwent abstract of SU 514111A, Acc. No. 1977–A3525Y, "Mode Radial Axial Hydraulic Turbine Installation with Test Probe Holder at Lower Blade Ring", Patent–assignee: Lengd Metal WKS.

Partial International Search Report Mailed on Sep. 28, 2001.

OPTICAL PROBES AND METHODS FOR SPECTRAL ANALYSIS

REFERENCE TO RELATED APPLICATIONS

This application is a continuation in part of U.S. patent application Ser. No. 09/803,131, filed Mar. 9, 2001 now U.S. Pat. No. 6,753,966, U.S. patent application Ser. No. 09/354,497, filed Jul. 16, 1999 now abandoned, and U.S. patent application Ser. No. 09/426,826, filed Oct. 25, 1999 now U.S. Pat. No. 6,424,416. Each of the afore-mentioned patent applications is incorporated herein by reference in their entirety.

BACKGROUND OF THE INVENTION

Most analytical techniques used in industry include taking samples to the laboratory to be analyzed by time consuming procedures. For use in the field, e.g., on-site analysis, spectral analyzers have been gaining favor because of the potential speed of analysis and the fact that they often represent a non-destructive means of analyzing samples. Based on spectroscopy technology, it is possible not only to determine the characteristics of a sample surface, but often the constituent components beneath a sample surface.

Typically, in spectroscopic applications an optimal range of wavelengths is selected to irradiate a sample, where reflected or transmitted light is measured to determine the characteristics of the sample. Some samples, for example, are best analyzed using a near infrared spectrum of light while others are optimally analyzed using a range such as visible or mid infrared spectrum.

Many spectral analyzers utilize a narrow spot size to intensely irradiate a sample to be analyzed. Illuminating a sample with a highly intense incident light typically results in an easier collection of larger amounts of reflected light, thus improving system performance. Unfortunately, a narrow spot size can sometimes provide inaccurate measurements because a small spot may not be representative of the intended sample, particularly where the sample is heterogeneous in nature, such as, for example, grains, seeds, powders or and other particulate or suspended analytes. A narrow spot may unduly heat the sample, affecting the nature of the spectra.

SUMMARY OF THE INVENTION

The present invention relates to spectral analysis systems and methods for determining physical and chemical properties of a sample by measuring the optical characteristics of its transmitted and/or reflected light. In general, the systems and methods of the present invention are useful for examining the spectroscopic characteristics of materials, such as particles or liquids, though the systems may be used to characterize other materials such as suspensions of particles and even gases. In certain embodiments, the subject system may be used in connection with non-uniform material, e.g. consisting of components of different compositions, because the system of the present invention does not require the samples to be homogeneous in order to achieve reliable results.

However, in addition to characterizing heterogeneous materials, the subject systems can also be used to ascertain whether or when a mixture or a stream of material is sufficiently homogeneous or fulfils certain specifications with regard to content and/or particle size.

One aspect of the invention relates to a probe head for spectroscopic analysis of a sample material that minimizes the effects of surface reflection on the spectral analysis of the sample thereby improving the spectral analysis. In such embodiments, the invention provides a probe system for spectral analysis in industrial, drug manufacturing, chemical and petrochemical settings and the like. In one particular embodiment, the probe is used in situations with sample materials having a large component of surface reflections relative to light paths passing through particles or a bulk of sample material in a diffuse, scattering path.

In particular, the invention provides a probe head for use with a spectrometer to analyze a material, the probe head having: (i) a light source arranged to irradiate a sample volume of the material proximate the probe head, which source may be a lamp or other radiation source disposed in the probe head, (ii) an optical pick-up, arranged to receive light energy reflected or otherwise emitted from the sample in the irradiated sample volume and transmit the emitted light to the spectrometer for analysis, (iii) an optical blocking element positioned within the optical path between the light source and the optical pick-up to force the optical path into the sample volume, and (iv) a reference shutter for selectively blocking light emitted from the irradiated sample volume from reaching the optical pick-up to facilitate calibration. The optical blocking element can minimize direct surface reflections from the sample or from components of the probe head, such as, for example, a sample window positioned in contact with or proximate the material, relative to light passing through and reflecting from the material within the sample volume to thereby improve the accuracy of the analysis of the material. The light source may provide a suitably broad bandwidth of light for irradiating the sample, and in certain preferred embodiments, simultaneously with multiple radiation wavelengths. The light pick-up receives light reflected or emitted from a sample being irradiated, and is in optical communication with one or more detectors which measure the intensity of the reflected light, e.g., in a wavelength-dependent manner. The detector may be located distal to the probe head and the pick-up may be an aperture in the probe head connected with an optical fiber or other waveguide that communicates light reflected or emitted by the sample to the detector. Alternatively, the detector may be proximal to the irradiated sample, e.g., within the probe head, and the pick-up may simply be an aperture for permitting light being reflected by the sample to enter the probe head. The spectrometer may include one or more signal processing circuits, such as in the form of a computation subsystem, for processing signals outputted from the detector.

In one embodiment, a method of performing spectral analysis comprises the steps of irradiating a sample volume of the material with light from a light source, transmitting light emitted from the irradiated sample volume to an optical pick up that is optically connected to a spectrometer, forcing an optical path between the light source and the optical pick-up into the sample volume, and selectively blocking light emitted from the irradiated sample volume from reaching the optical pick-up to facilitate calibration of the spectrometer. The step of forcing the optical path may include blocking light reflected from a sample window within the optical path from reaching the optical pick-up. The step of selectively blocking light may include selectively moving a reference shutter into the optical path to block light emitted from the irradiated sample volume from reaching the optical pick-up.

Another aspect of the invention relates to a probe head for use with a spectrometer to analyze a material. The probe head may comprise a housing having a first chamber separated from a second chamber, a light source disposed in the first chamber and arranged to irradiate a sample volume of the material with a plurality of wavelengths of light, a wavelength separator disposed in the second chamber, the wavelength separator receiving light reflected from the irradiated sample volume to produce spatially separated light of different wavelengths, and a detector connected to the spectrometer. The detector is preferably disposed in the second chamber and positioned to receive the spatially separated light from the wavelength separator. The detector operates to transmit a signal to the spectrometer representative of the intensity of the spatially separated light received from the wavelength separator.

The first chamber of the housing may include a first window and the light source irradiates light through the first window onto a sample volume. Additionally, the second chamber of the housing may include a second window and the wavelength separator receives light through the second window from the irradiated sample volume. A reflector may be positioned in the housing to reflect a portion of light emanating from the light source into the second chamber for calibration measurements. The probe head also may include a reference shutter for selectively blocking light emitted from the irradiated sample volume from reaching the detector to facilitate calibration of the spectrometer and a diffuser for diffusing light reflected from the irradiated sample volume into the wavelength separator.

In certain embodiments the detector of the probe head may have a larger viewing aperture, for example, greater than about 0.5 square inches and, preferably, between about 0.5 square inches and about 10 square inches. Additionally, in certain embodiments, the light source may illuminate a larger spot size, for example, greater than about 0.5 square inches, and preferably, between about 0.5 square inches and about 10 square inches.

Another aspect of the invention relates to a probe head for use with a spectrometer that facilitates the spectral analysis of a material flowing in a sample containment apparatus, such as, for example, grain or other agricultural product flowing in a duct. The probe preferably includes a housing that is configured for positioning on a sample containment apparatus to monitor a material flowing through the sample containment apparatus.

As will be understood, there are a wide variety of materials for which the systems and methods of the present invention can be used for characterization. Without intending to be limiting, exemplary materials include:

vegetable foods, such a wheat, corn, rye, oats, barley, soybeans, amaranth, triticale, and other grains, rice, coffee and cocoa, which may be in the form of whole grains or beans, or a ground or comminuted product (analysis for protein, starch, carbohydrate and/or water), seeds, e.g. peas and beans, such as soybeans (analysis for protein, fats and/or water), products mainly consisting of or extracted from vegetable raw materials, such as snacks, dough, vegetable mixtures, margarine, edible oils, fibre products, chocolate, sugar, syrup, lozenges and dried coffee extract (powder/granulate), animal foodstuffs, such as dairy produce, e.g. milk, yogurt and other soured milk products, ice cream, cheese (analysis for protein, carbohydrate, lactose, fat and/or water), meat products, e.g. meat of pork, beef, mutton, poultry and fish in the form of minced or emulgated products (analysis for protein, fat, water and/or salts) and eggs, which foodstuffs may be present in a completely or partly frozen condition, fermentation broths, such as alcoholic beverages, e.g. wine or beer, fodder, e.g. pellets or dry/wet fodder mixtures of vegetable products, fats and protein-containing raw materials, including pet food, manure and compost, including composting garbage, grass clippings, pharmaceutical products, such as tablets, mixtures, powders, creams and ointments, biological samples including, for example, biological fluids such as blood, urine, spinal fluid, saliva, etc, and tissue samples, and technical substances, e.g. wet and dry mixtures of cement and mortar, plastics, e.g. in granular form, mineral materials, such as solvents and petrochemical products, e.g. oils, hydrocarbons and asphalt, solutions of organic or inorganic substances, e.g. sugar solutions, glue and epoxies, and liquids with light scattering properties in suspension, slurries, fluidized materials including both solid and liquid and similar entities.

The components comprising the systems of the present invention are preferably integrated into a single unit, e.g., to create either a portable spectral analyzer or one which is readily disposed along a path of a moving material.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF EXEMPLARY EMBODIMENTS

Figure 1:
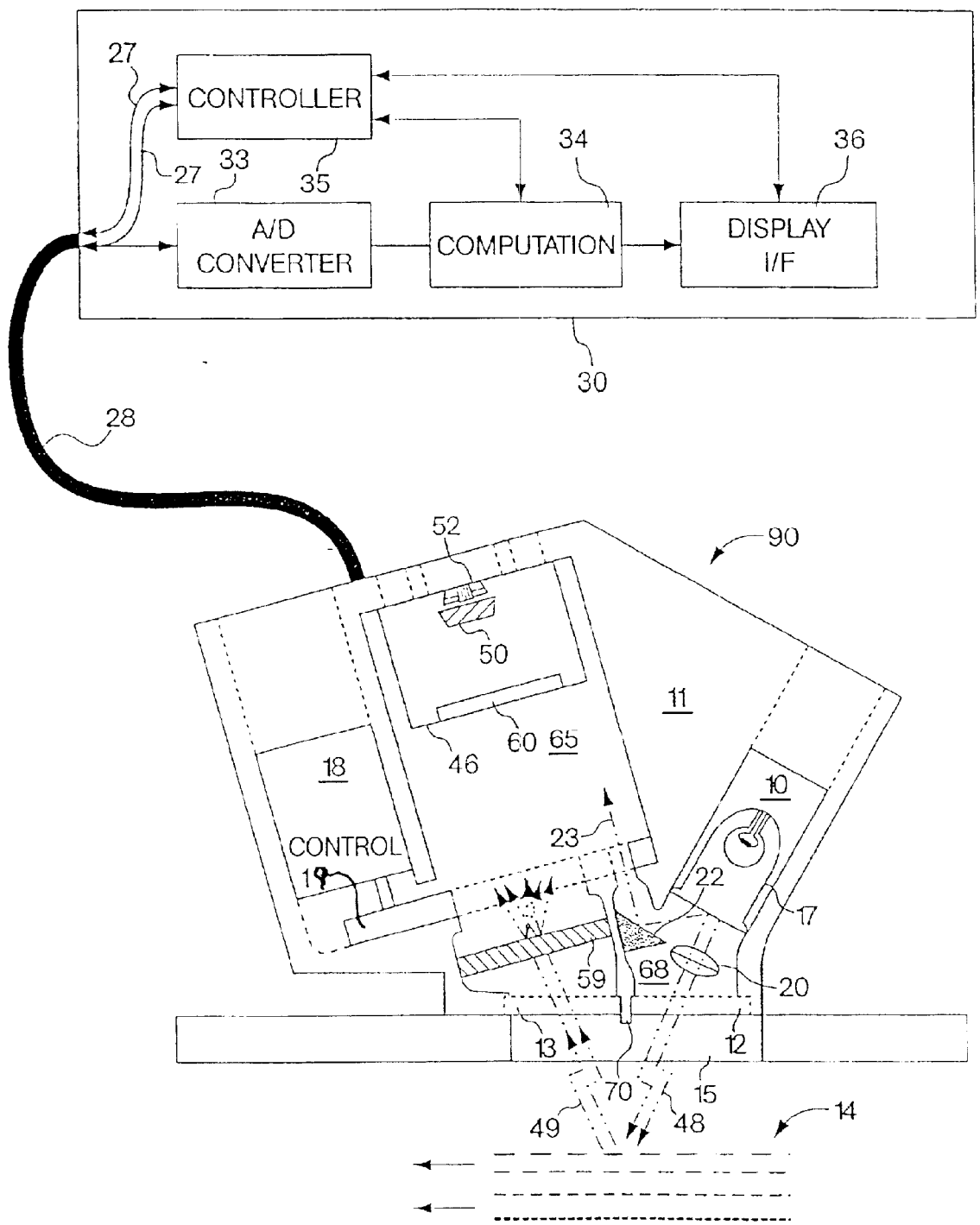
FIG. 1 is a schematic illustration of a spectral analyzer, according to the present invention.

FIG. 1 illustrates a probe head 90 for analyzing the constituent or color components of a sample 14, in accordance with one exemplary embodiment of the present invention. The probe head 90 uses a suitable continuous or pulsed irradiating light source 10. Radiation from the light source 10 shines forward through a first window 12 to the surface of a sample 14. The light source 10 simultaneously produces light of multiple wavelengths in a region of interest. Depending on the application, the present invention supports wavelength analysis in a range of UV, visible, and infrared wavelengths. The actual range of light used in a particular application depends on the wavelength response of the detector, which is matched with a light source capable of emitting such wavelengths.

The desired range of wavelengths to be analyzed dictates the type of detector used in the present invention, which typically is wavelength limited. For example, a fairly inexpensive silicon photodiode or charge coupled device (CCD) array is capable of detecting light intensities of wavelengths between 400 and 1100 nanometers. Other detectors optionally used in the invention are lead sulfide and lead selenide detectors, which support a response between 1000 to 3000 nanometers and 3000 to 5000 nanometers respectively. Optionally, other detectors used in the invention for near-infrared radiation include silicon, germanium, InGaAs, PMTs (Photo-Multiplier Tubes), and microbolometers.

The light source 10 is positioned to shine upon the sample 14 to be analyzed. Preferably, the light source 10 is a quartz halogen or tungsten filament bulb and is widely available.

The light source 10 and related components are preferably positioned within a suitable housing 11. In such an instance, a first window 12 is disposed between the light source 10 and the sample 14 to be analyzed. This prevents debris from entering the cavity and obstructing the illuminating light source 10. The first window 12 is formed of a suitable material, such as sapphire or glass, which is transmissive at the wavelengths of interest, and which does not see a significant absorption shift due to temperature changes. Sapphire also resists scratching and, therefore, debris brushing against its surface will not damage the window.

The housing 11, including the enclosed light source 10, first window 12, and other related components to be described, is thus positioned to monitor the sample 14 to be analyzed. This is accomplished by positioning the housing 11 such that light radiating from the light source 10, shines through the first window 12 onto the sample 14.

The housing 11 can be positioned such that the first window 12, as well a second window 13, contact an observation window 15, which may be a part of a preexisting window in a sample containment apparatus, e.g. an observation window in a vat, bin, conveyance, or the like. Alternatively, the first window 12 and the second window 13 may be positioned directly within an aperture formed in the sample containment apparatus, eliminating the need for the observation window 15.

A parabolic mirror or reflector 17 may be disposed within the light source cavity to direct light from the light source 10 to the sample 14 being analyzed. In the preferred embodiment, the light emanating from light source 10 is either collimated or focused to enhance the intensity of the light reflected off the sample. However, a lens 20 may optionally provide a means of additionally focusing or defocusing the light into a more or less intense beam. In other words, the irradiated light shining on the sample 14 is optionally focused to enhance the source.

In an alternate embodiment, more than one light source 10 can be used, such as an array of e.g., semiconductor lasers or light emitting diodes, preferably focused on the same point in the sample. Alternatively, an arrangement of bulbs or other light sources may be employed, such as, for example, a ring of tungsten filament bulbs or quartz halogen bulbs.

It is preferred that the light source 10 be placed such that it directly illuminates the sample 14 to be analyzed through the first window 12 with no fiber optic or other device other than the first window 12 itself being disposed between the light source 10 and the sample 14.

In a preferred embodiment, the illumination spot size from the light source 10 onto the sample 14 is approximately 1 to 3 inches in diameter, creating a spot of light between 0.5 and 10 square inches. Effectively, the incident light 48 shines through the first window 12 onto the sample 14 to produce reflected light 49 directed towards the second window 13 and an analysis chamber where light intensities are analyzed. Such a wide illumination spot size and corresponding viewing aperture is preferred because it results in more accurate measurements of the sample 14 to be analyzed. This is due to the fact that small inhomogeneities relative to the larger spot size within a sample region are typically negligible with respect to the whole. In other words, the wider spot size produces a better averaging effect because a potential inhomogeneity in a sample is not at the focus of the illumination spot.

Without a wide viewing aperture, calorimeter and constituent measurements based on small spot sizes can produce inaccurate results if the operator of such a device erroneously takes a sample measurement of an inhomogeneity in the sample not representative of the whole. For example, a small black spot on a dark blue background barely detectable by the naked eye could fool an operator that the color of the sample is black rather than blue. The above-described probe embodiments help to reduce erroneous colorimeter measurements by advantageously including a wider illumination spot size and viewing detector to support the aforementioned color averaging effect.

Spectral analyzers available in the market often incorporate costly optical hardware for receiving the light reflected off a sample and directing it to an optical detector located at a distance. To view even a small spot with these systems requires a high intensity light source. This method of using optical hardware to redirect the reflected sample light 49 limits the spot size to a narrow diameter because the reflected light must be focused into a small fiber optic cable.

The exemplary embodiment described, on the other hand, advantageously positions a detector 52 with a wide viewing aperture located in a second chamber 65 immediately adjacent the first chamber 68 to receive the reflected sample light 49. This can eliminate the need for costly fiber optic hardware because received light no longer needs to be directed to a detector at a remote location. Rather, reflected sample light 49 naturally strikes a detector 52 located immediately in the second chamber 65. To match the performance of the present probes, a fiber system would require a very large fiber bundle for redirecting reflected sample light to a remote detector.

Although a wider viewing aperture and spot size is preferred, one skilled in the art, however, will appreciate that alternative sizes for the viewing aperture and/or the spot size, including smaller sizes, may be employed without departing from the scope of the present invention.

An optical blocking element 70 also serves to separate the first and second windows 12 and 13 and to force the optical path of the light source 10 and the detector 52 into the sample 14. In this manner the incident light 48 and the sample light 49 intersect within the sample 14 and thereby discriminate against (i.e., prevent) direct surface reflection by inhibiting light directly reflected from the first window 12 and from the surface of the sample at the window 12 from reaching the detector 52.

Eliminating the fiber optic pickup and associated fiber optic cables has advantages in addition to enabling the use of a wider illumination spot size. Typically, fiber optic cables have a limited transmission bandwidth. Hence, when they are used to steer reflected light to a detector located far away, the spectral range of directed light is limited to the transmission bandwidth of the cable. Moreover, the use of fiber optic cables is further prohibitive because the fiber optic cables supporting the wavelengths of mid infrared are particularly expensive and have large throughput losses associated with them. In some cases, just a few meters of this type of cable can be more than a thousand dollars. The exemplary probe head 90 illustrated in FIG. 1 is not as bandwidth limited nor burdened with unnecessary additional cost because it need not incorporate any fiber optic cables to transmit light.

The use of a fiber optic cable to transmit the reflected sample light 49 is additionally undesirable because the integrity of the optical signal within a fiber optic cable is susceptible to heat distortion and mechanical vibrations. This is especially true when the fiber optic cable supports the transmission of light in the infrared region. Both the heat distortion and mechanical vibrations, particularly prevalent in a portable device, negatively impact the integrity of the mode structure of the optical signal used to detect constituents in a sample. By placing the detector 52 in a second chamber 65 immediately adjacent the light source 10 without incorporating an optical fiber in the reflected sample light path 49, the probe head 90 advantageously avoids the aforementioned problems.

The probe described above replaces the small fiber, which typically has an aperture area of less than 1 square millimeter, with a large viewing aperture of typically 0.5 to 10 square inches. This allows for viewing large fields of view with low light intensities. With additional optics, the aperture size can be adjusted to create a variable field of view and allows a large sample to be imaged from a distance.

Continuing to refer to FIG. 1, light emitted by the light source 10 passes through the first window 12 into the sample 14 to be analyzed. Incident light 48 from light source 10 then reflects off the sample 14, where the reflected sample light 49 is angularly directed back through second window 13.

In a preferred embodiment, the angle of the light source 10 and detector unit 52 in the second chamber 65 are optimized so that most of the reflected sample light 49 is directed to the second chamber 65 for spectral analysis of the sample 14. For example, the light source 10 may be optimally angled at approximately 60° relative to the first window 12 while the detector unit 52 in the second chamber 65 may be angled at approximately 60° relative to the second window, as shown in illustrative FIG. 1.

The first and second window 12, 13 are preferably parallel and in the same plane as shown. However, other embodiments optionally include windows that are positioned at an angle with respect to each other, while the first and second chamber 65, 68 are still positioned adjacent to each other.

The second chamber 65, as mentioned, includes optical devices for detecting the reflected sample light 49. Specifically, the reflected sample light 49 passes through the second window 13 into the second chamber 65 where it is spectrally analyzed. Diffuser 59 acts to scatter the reflected sample light 49, spatially distributing the intensity of the light throughout the second chamber 65 for more accurate simultaneous spectral readings and to prevent imaging of the sample. For example, reflected sample light 49 of various wavelengths is more evenly distributed throughout the second chamber 65. Otherwise, high intensity light regions caused by reflected sample light 49 results in less accurate constituent measurements due to imaging effects.

Hermetically sealed chamber 46 may be positioned in the second chamber 65 to receive reflected sample light 49. An optically transmissive third window 60 allows diffused light emanating from the diffuser to shine onto wavelength separator 50 and array detector 52 (e.g., CCD), both of which are positioned within the hermetically sealed chamber 46. This airtight chamber protects sensitive optical components from corrosive and measurement-inhibiting elements such as humidity and dust. Without the hermetically sealed chamber 46, a buildup of dust and other debris on the detection unit 52 and wavelength separator 50 will negatively effect constituent measurements. It should be noted that all, none or part of the second chamber 65 is optionally designed to be hermetically sealed.

The wavelength separator 50 within hermetically sealed chamber 46 in a preferred embodiment provides spatial separation of the various wavelengths of diffusely reflected light energy of interest. Suitable wavelength separators 50 include linearly variable filters (LVF), gratings, prisms, interferometers or similar devices. The wavelength separator 50 is preferably implemented as a linearly variable filter (LVF) having a resolution ($\Delta\lambda/\lambda$, where $\lambda$ is the wavelength) of approximately one to four percent.

The now spatially separated wavelengths in turn are fed to the detector 52. The detector 52 is positioned such that it simultaneously measures the response at a broad range of wavelengths. In the preferred embodiment, the detector 52 is an array of charge-coupled devices (CCDs), which individually measure the light intensity at each of the respective wavelengths. In other words, each cell of the CCD array is tuned to measure the intensity of an individual bandpass of light.

Other suitable detectors 52, however, can be constructed from fast scan photodiodes, charge injection devices (CIDs), or any other arrays of detectors suitable for the task of simultaneously detecting the wavelengths of interest.

In a preferred embodiment, the detector 52 is a silicon CCD array, such as a Fairchild CCD 133A available from Loral-Fairchild or a similar silicon CCD array available from Reticon. This CCD array 52 is a 1,024-element array processing wavelengths in the range from about 570 to about 1120 nm. As mentioned, other detectors supporting different bandwidths are optionally used.

In addition, the detector 52, such as a CCD array, is typically temperature sensitive so that stabilization is usually preferred. Cooling is achieved using a thermoelectric cooler.

The preferred embodiment of the present probe also includes a reflector 22 disposed in the first chamber to reflect reference photons 23 to the wavelength separator 50 and detector 52 positioned in the second chamber 65 depending on the position of the light blocking shutter 19, discussed below. The reflector 22 is preferably fixed such that repeated measurements are based upon the same reference light intensity.

A light blocking shutter 19 is provided to selectively allow the appropriate light to flow into the second chamber 65. Shutter 19 controls the passage of either sample light 49 into the second chamber 65, or the passage of reference light 23 reflected off reference light reflector 22 into the second chamber 65. The second shutter 19 can also be used to block all incoming light for measuring a "dark" reference signal. Shutter 19 can also be implemented as a dual shutter mechanism, as will be understood by one of skill in the art.

Control electronics and shutter motor 18 located adjacent to the second chamber 65, provide a mechanism for controlling light into second chamber 65. Shutter position commands are received via electronic signals transmitted by controller 35 residing in the electronics block 30.

Light blocking shutter 19 is appropriately positioned for each of three measurements. A first measurement involves blocking both the reflected sample light 49 and reference photons 23. This reference measurement of the "dark" second chamber 65 serves as a means of calibrating the detector unit or array 52. A second measurement involves blocking the reflected sample light 49 and measuring the reference photons 23. This measurement serves to calibrate the system to the light source 10. Finally, a third measurement involves blocking the reference rays 23 and measuring the reflected sample photons 49. Details of the measurements and related computations are further described in FIG. 2.

The electronic signals 27 are bundled together in a wire harness 28 connecting the probe head housing 11 and electronics block 30. In a practical deployment of the probe head 90, it is preferred that the electronics block 30 be as close as possible to housing 11. However, in some applications it may be preferable to separate the probe head 90 and electronics block 30.

The electronics block 30 includes an analog to digital converter 33, a constituent computation function 34, a controller 35, and a display interface 36. In the preferred embodiment, the computation function 34, controller 35 and display interface 36 are implemented as software in a computer, microcontroller, microprocessor and/or digital signal processor. Electronic signals 27 in wire harness 28 provide connectivity between the electronics in the probe head housing 11 and the electronics block 30.

As mentioned, one application of the systems of the present invention involves mounting the electronics block 30 in a shielded environment, such as a cab, while the probe head 90 is mounted in a position to detect the sample 14 to be analyzed. Therefore, based on this separation, the electronics are designed to ensure that signal integrity does not suffer because of the length of the wire harness 28. For example, the electronic signals 27 within wire harness 28 are properly shielded to prevent excess coupling noise, which may deleteriously effect A/D readings of the CCD array detector 52. The controller 35 coordinating the A/D sampling process, as mentioned, controls the shutter mechanisms positioned in the second chamber 65 for the various spectral measurements.

The individual electrical signals provided by the CCD for each wavelength are then fed from the output of the detector 52 to analog to digital converter 33 where the electrical signals are converted to digital signals for processing.

A computation block 34, preferably implemented in a microcomputer or digital signal processor as described above, then carries out calculations on the basis of the received wavelength intensities to obtain either the color characteristics or percentage concentrations of constituents of the sample 14. The results of the sample analysis are then communicated to an operator in any desired way such as by a meter or presenting them to a display. The display is optionally integral to a laptop computer or display, such as an LCD, on or near the electronics block 30 or probe head 90. The computation block may be part of the electronics block 30 or may be physically separated from it.

In one exemplary embodiment, the electronics block 30 and probe head 90 are integrated to produce a handheld portable spectral analyzer. This embodiment is particularly beneficial in colorimeter applications that require analyzing the sample in a fixed location such as a home where, for example, wallpaper or paint is fixed to a wall. Based on its portability, the analyzer is easily maneuvered to test samples in awkwardly tight spaces. Additionally, because of its small size, it is less likely to be damaged or dropped during transit or use.

The analyzer may also support calculating constituent concentrations in samples such as grain. Techniques for calculating percentage concentrations of grain based upon samples of light and particular wavelengths include the multi-variate techniques detailed in the book by Sharaf, M. A., Illman, D. L., and Kowalski, B. R., entitled "Chemometrics" (New York: J. Wiley Sons, 1986).

Preferred wavelengths of interest depend upon the constituents being measured. For example, when measuring protein concentration, the methods make use of absorptance attributable to the vibration-rotational overtone bands of the sub-structure of protein. At longer wavelengths absorption coefficients are large, the path length is short, and thus one would not sample the interior of the grain particles. At shorter wavelengths the absorption coefficients are small and the signal is thus weak.

The probe head 90 provides for irradiation of the sample followed by spatial separation and detection of multiple wavelengths in parallel, making for rapid analysis of this sample. Moreover, since the optical portions of the unit are substantially insensitive to vibrations, the probe head 90 may be deployed in environments where real time analysis of samples is performed in harsh environments.

Furthermore, the use of the CCD array as detector unit 52 provides advantages over prior art techniques that use discrete or scanned diode arrays. In particular, the CCD bins are all filled with charge at the same time in parallel with one another. They are then emptied and the results read out by the controller 35 are processed while the CCD array begins filling again. Based on sampling over a time period, each pixel or bin detects reflected light intensities off the sample over the same time interval. This is particularly important if the sample happens to be moving across the viewing region of the device. In contrast, diode arrays must be read sequentially so that for example, any given element is producing a signal from the sample that is distinct from those seen by previous pixels.

The signal to noise ratio of the probe head 90 measurements may be improved by averaging over the course of many measurements.

Figure 2:
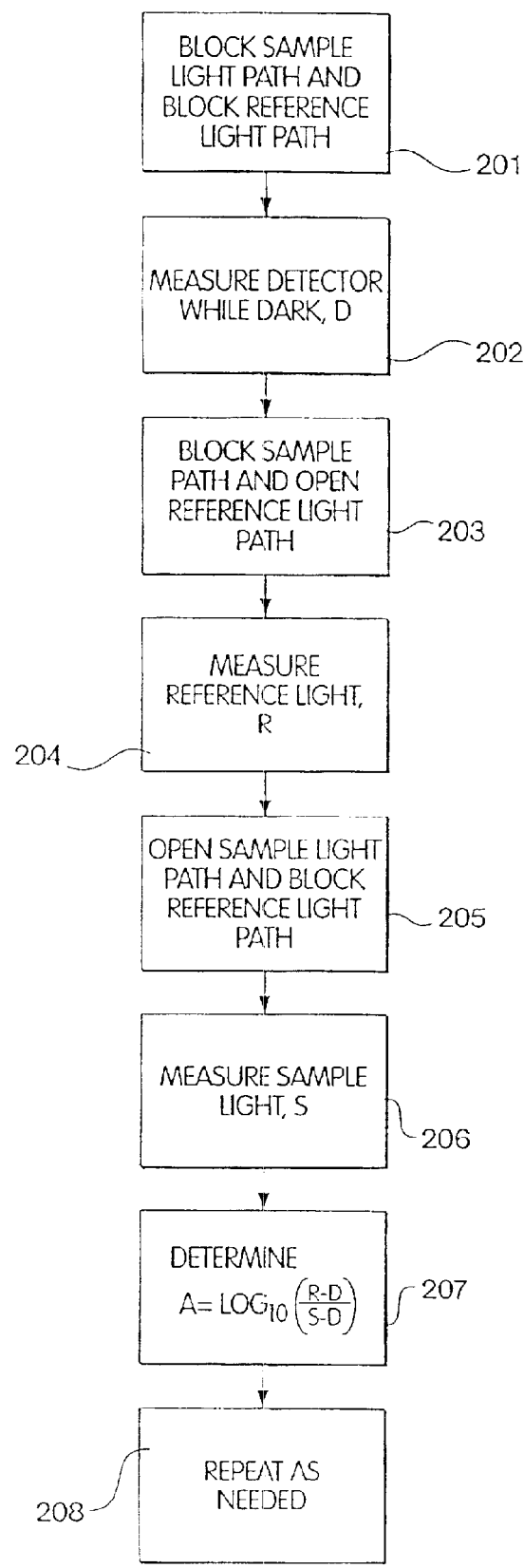
FIG. 2 is a flow chart depicting a process for measuring absorptivity of a sample according to the principles of the present invention.

One exemplary absorption measurement includes the following process illustrated in FIG. 2:

1. Block both the sample reflection light and reference light from the wavelength detector unit (step 201).
2. Perform a reading on the wavelength detector unit, storing measurement data in D for dark spectrum (step 202).
3. Block the sample reflection light and allow reference light to shine on wavelength detector unit (step 203).
4. Perform a reading on the wavelength detector unit, storing measurement data in R for reference light spectrum (step 204).
5. Block the reference light and allow sample reflection light to shine on wavelength detector unit (step 205).
6. Perform a reading on the wavelength detector unit, storing measurement data in S for sample spectrum (step 206).
7. Calculate the absorptance spectrum A, where the light absorption as derived from these diffuse reflectance measurements is given by:

$$A = \mathrm{LOG}_{10}(R-D)/(S-D)\,(\text{step } 207).$$

8. The process may repeat as needed (step 208).

Further data processing therefore may provide a second derivative of absorptance spectrum A to remove constant and linear offsets so that only quadratic and higher order features in the absorptivity spectrum are utilized in the determination of protein content. In addition, since the absorptivity variations from the presence of protein are quite small, multiple realizations, averaging, and second derivative analysis are typically used to produce the desired absorptivity number at a particular wavelength.

Figure 3A:
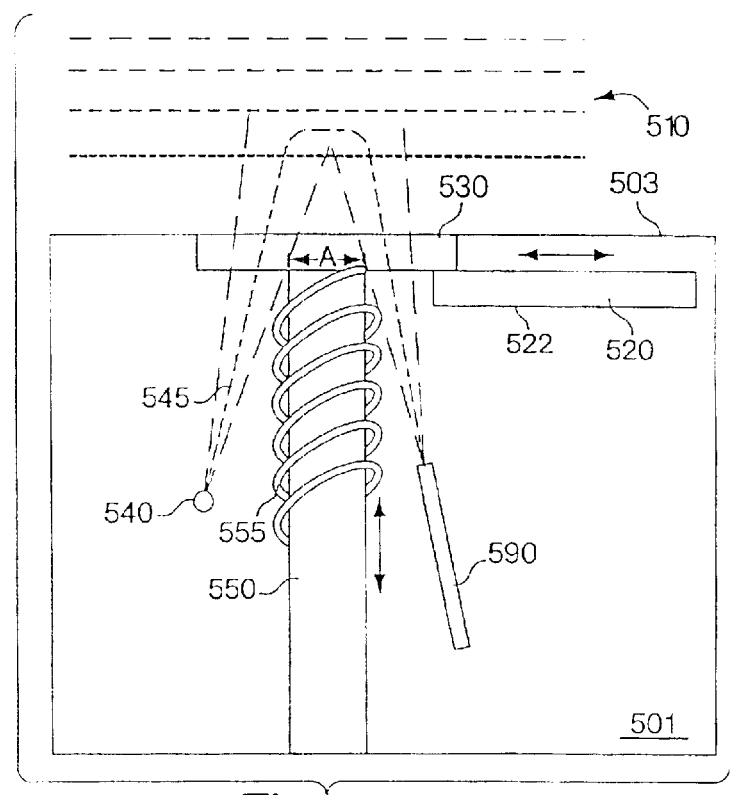
FIGS. 3A and 3B are schematic illustrations of an alternative embodiment of an optical probe head of the present invention.
Figure 3B:
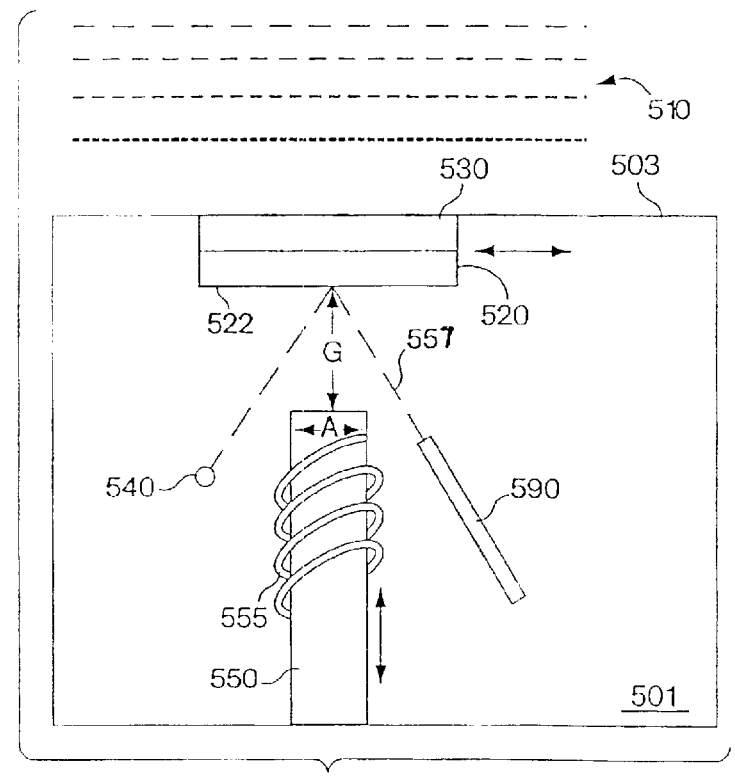

An alternative embodiment of a probe head for use with a spectrometer to analyze material is illustrated in FIGS. 3A and 3B. The probe head 501 is particularly useful for analyzing materials having diffuse reflecting properties such as powders, slurries, etc. The probe head 501 includes a light source 540 for irradiating a sample volume of the material 510 proximate the probe head 501 through a window 530 formed in the probe head 501. The light source 540 may be a lamp or other radiation source disposed in the probe head 501, or it may be the radiant end of an optical fiber or other waveguide delivering light from a source distal to the probe head 501. Alternatively, more than one light source 540 may be used, such as an array of e.g. semiconductor lasers or light emitting diodes or an arrangement of lamps or other light sources, such as, for example, a ring of tungsten filament bulbs or quartz halogen bulbs. The window 530 may be formed of a suitable material, such as sapphire or glass, which is transmissive at the wavelengths of interest, and which does not allow for a significant absorption shift due to temperature changes.

The probe head 501 may also include an optical pick-up, such as, for example an optical fiber 590, arranged to receive light emitted from the sample in the irradiated sample volume and transmit the received light to, for example, a spectrometer, for analysis. The optical fiber 590 may be a single fiber or a multiple fiber bundle capable of both incoherent and coherent waves. The optical fiber 590 may be made from quartz, glass, plastic or other transmitting materials. Preferably, the optical fiber 590 has a numerical aperture of 0.2 to 0.5. Optionally, the optical fiber 590 can be hollow, with adequately reflecting walls. Alternatively, the optical fiber 590 may be replaced in situ by a detection system, such as, for example, in the manner of the probe head described above in connection with FIG. 2.

The probe head 501 may be constructed out of metals such as stainless steel, steel or aluminum; or made from moldable and durable plastic; or other materials. The materials may be translucent, transparent, or opaque and may be chosen for ease of cleaning and maintenance. The probe head 501 can also be constructed of material that optimizes the appropriate measurements of the sample material. The exterior surface 503 of the probe head 501 may be geometrically shaped to optimize the probe measurements.

The exemplary probe head 501 may also include an optical blocking element 550 positioned in the optical path between the light source 540 and the light collecting optical fiber 590. The optical blocking element 550 forces the path of light into the material 510 thereby reducing error due to surface reflection and increasing the signal to noise ratio of the spectral analysis. The optical blocking element 550 is opaque and preferably is in contact with or effectively splits/bifurcates the window 530. The optical blocking element 550 may be constructed out of metals such as stainless steel, steel or aluminum; or made from moldable and durable plastic; or other opaque materials. In one preferred embodiment, the optical block element 550 is biased into contact with the window 530 by spring loading, via a spring 555 or by other biasing mechanisms.

A typical, theoretical light path 545 is shown in FIG. 3A to illustrate an optical path of light into and reflected from the material 510 during data collection. The optical block element 550 effectively minimizes the direct surface reflection from the window 530 or the material 510 by blocking such direct surface reflection from reaching the optical fiber 590. In this manner, the allowed optical paths, including theoretical optical path 545, originates from light source 540, undergoes diffusive transport in the material 510, and is collected and transported within the numerical aperture of the optical fiber 590.

The probe head 501 may include a reference shutter 520 for calibrating or re-normalizing the spectrometer, in particular the signal processing algorithm of the spectrometer, to account for any signal changes relative to previous calibrations of the spectrometer. The reference shutter 520 includes a reflective surface 522 having a reasonably uniform value of reflectance over the wavelength of interest. To be effective for calibration, the reflectance value of the reflective surface preferably remains unchanged with regards to time, temperature, usage, etc. The reflective surface 520 may be made out of, or coated by, stable reflective materials such as gold, white ceramics, Spectralon®, stable white paint, and other such materials.

The reference shutter 520 is movable between an open, measurement position, illustrated in FIG. 3A, and a closed, calibration position, illustrated in FIG. 3B. In the open, measurement position, the reference shutter 520 is positioned out of the optical path between the light source 540 and the optical fiber 590 to facilitate spectral analysis of the material 510. In the closed, calibration position, the reference shutter 520 is positioned in the optical path between the light source 540 and the optical fiber 590 to effectively block light from the sample material 510 from reaching the optical fiber 590. As shown in FIG. 3B by illustrative, theoretical optical path 557, light from the light source 540 reflects off the reflective surface 522 to the optical fiber 590. The reference shutter 520 may be moved between the closed and open positions by a rotary solenoid, or by other electromagnetic, electromechanical, or mechanical mechanisms.

During calibration of the system, it is preferable that the optical blocking element 550 be moved away from the window 520 to allow the reference shutter 520 to move into the closed position, as illustrated in FIG. 3B. Preferably, the optical blocking element 550 is moved a distance from the window 520, e.g., gap G in FIG. 3B, such that sufficient light from the light source 540 can reflect from the reflective surface 522 of the shutter 520 and reach the optical fiber 590 at an angle within the numerical aperture of the optical fiber 590. The optical blocking element 550 can be moved towards and away from the window 530 by a rotary solenoid, or by other electromagnetic, electromechanical, or mechanical mechanisms. Alternatively, the movement of the optical blocking element 550 can be mechanically coupled to the movement of the shutter 520, as discussed below, such that separate movement mechanisms, e.g. solenoids, for the optical blocking element 550 and the shutter 520 are not necessary.

Figure 4:
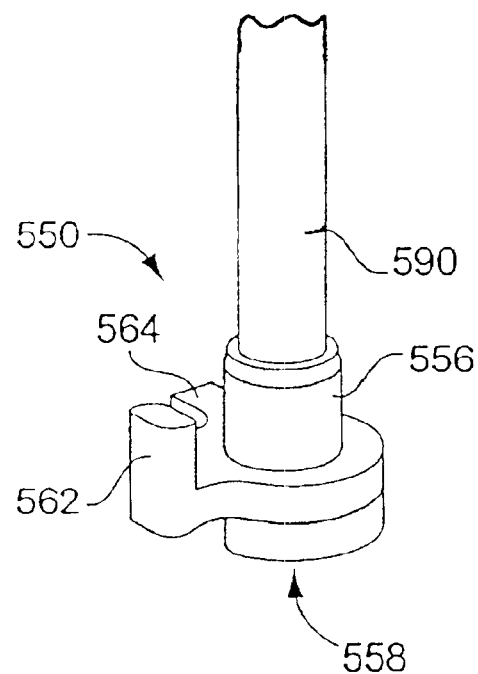
FIGS. 4A and 4B are perspective views of one embodiment of the optical blocking element of the probe head of FIGS. 3A and 3B.
Figure 4:
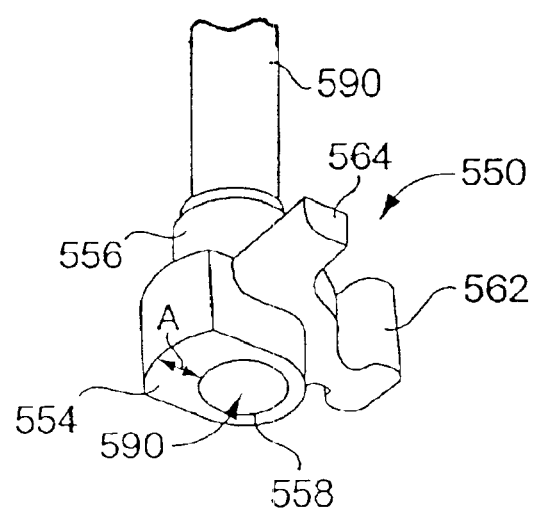
Figure 5:
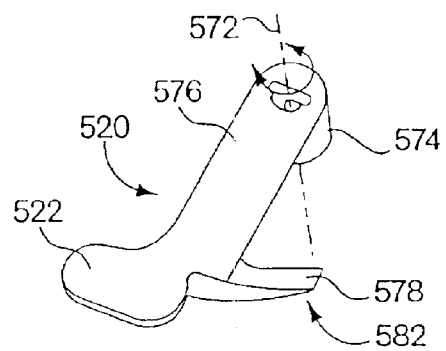
FIGS. 5A and 5B are perspective view of one embodiment of the reference shutter of the probe head of FIGS. 3A and 3B.
Figure 5:
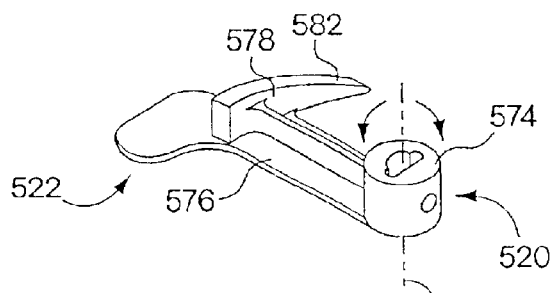
Figure 6:
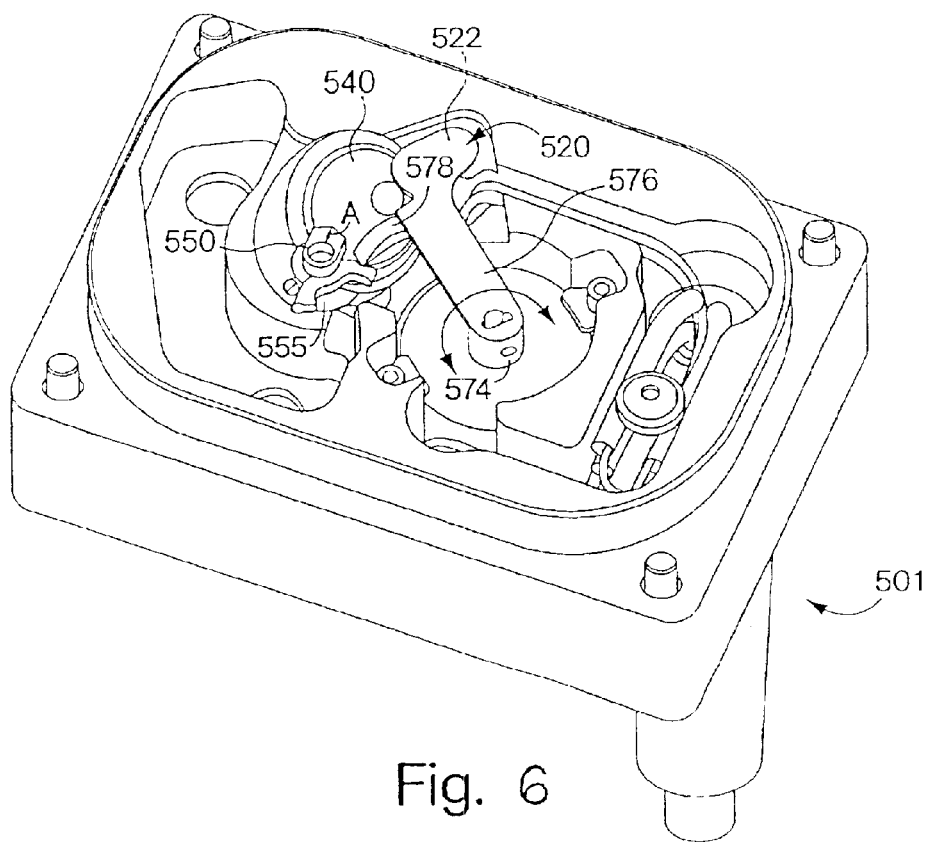
FIG. 6 is a perspective view of an optical probe head implementing the optical blocking element and the reference shutter of FIGS. 3A–B and 4A–B, respectively, illustrating the probe head with the sample window removed.

FIGS. 4–6 illustrate an exemplary, preferred embodiment of the probe head 501. FIGS. 4A and 4B, illustrate a preferred embodiment of the optical blocking element 550. The exemplary optical blocking element 550 includes a blocking surface 554 for contacting the window 530 and a cylindrical housing 556 for attachment to the optical fiber 590. The cylindrical housing 556 includes an opening 558 for allowing light to enter the cylindrical housing and reach the optical fiber 590. Spring 555, as shown in FIG. 6, can be seated about the exterior of the housing 556 to bias the blocking surface 554 into contact with the window 530. The blocking surface 554 is sized and shaped to effectively block light directly reflected from the window 530 and the surface of the sample material 510. In particular, the width A of the blocking element 550, illustrated in FIG. 4A, is preferably optimized for the material 510 being probed and for the position of the light source 540 and the optical fiber 590 within the probe head 501, to minimize and, preferably completely block, light directly reflected from the window 530 and the surface of the material from reaching the optical fiber 590.

The optical blocking element 550 may include an arm 564 extending perpendicularly from the longitudinal axis of the housing 556, and thus, the optical fiber 590, and is provided to contact a camming surface of the shutter 520 to facilitate linear movement of the optical blocking element 550 when the reference shutter 520 is moved into the closed position, as discussed in more detail below. A second arm 562 may be included to be contained within a slot within the probe head 501 to prevent axial rotation of the optical blocking element 550.

An exemplary embodiment of the shutter 520 is illustrated in FIGS. 5A and 5B. The exemplary shutter 520 is configured for rotational movement about a rotation axis 572. The shutter 520 includes a cylindrical hub 574 that can be coupled to a rotary solenoid and an arm 576 that extends from the hub 574 in a direction perpendicular from the hub 574. The arm 576 is generally planar in shape and includes the reference surface 522 formed at the end distal from the hub 574. The reference surface 522 of the shutter 520 can thus be rotated about the rotation axis 572 between the open and closed position.

A camming arm 578 is provided proximate the reference surface 522 and extends generally perpendicular to the longitudinal axis of the arm 576. The camming arm 578 includes a camming surface 582 for engaging the arm 564 of the optical blocking element 550 in a camming relationship. As the shutter 520 rotates the reference surface 522 from the open position, illustrated in FIG. 3A, to the closed position, illustrated in FIG. 3B, the camming surface 582 engages the arm 564 of the optical blocking element 550 to move the blocking surface 554 out of contact with the window 530. Thus, the camming surface 582 translates the rotational motion of the shutter 520 into axial motion along an axis generally perpendicular to the window 530.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A probe head for use with a spectrometer to analyze a material, the probe head comprising:

a light source arranged to irradiate a sample volume of the material proximate the probe head and thereby irradiate any material disposed in the same volume, an optical pick-up arranged to receive light emitted from the irradiated sample volume and transmit the emitted light to the spectrometer for analysis, an optical blocking element positioned in the optical path between the light source and the optical pick-up to force the optical path into the sample volume, and a reference shutter for selectively blocking light emitted from the irradiated sample volume from reaching the optical pick-up to facilitate calibration of the spectrometer; and a housing that includes a sample window, into contact with which the blocking element is biased, which window is so positioned with respect to the light source, the sample volume, and the optical pick-up that the light source irradiates the sample volume through the sample window, and the light emitted from the sample volume to the optical pick-up travels through the sample window.

2. The probe head of claim 1, wherein the optical blocking element is opaque.

3. The probe head of claim 1, wherein the reference shutter is movable between a closed position that blocks light emitted from the sample volume from reaching the optical pick-up and an open position that permits light emitted from the sample volume to reach the optical pick-up.

4. The probe head of claim 3, wherein movement of the reference shutter from the open position to the closed position causes the optical blocking element to move out of contact with the sample window.

5. The probe head of claim 1, wherein the reference shutter includes a reference surface having a uniform reflectance value to facilitate calibration of the spectrometer.

6. A method of spectroscopically analyzing a material comprising:

irradiating a sample volume of the material with light from a light source, transmitting light emitted from the irradiated sample volume to an optical pick up that is optically connected to a spectrometer, forcing an optical path between the light source and the optical pick-up into the sample volume, so positioning an optical blocking element as thereby to inhibit reflections from a sample window within the optical path from reaching the optical pick-up, selectively blocking light emitted from the irradiated sample volume from reaching the optical pick-up to facilitate calibration of the spectrometer.

7. The method of claim 6, wherein the step of selectively blocking light includes selectively moving a reference shutter into the optical path to block light emitted from the irradiated sample volume from reaching the optical pick-up.

8. A probe head for use with a spectrometer to analyze a material, the probe head comprising:

a housing having a first chamber, which includes a solid transparent first window and is separated from a second chamber, which includes a solid transparent second window, a light source disposed in the first chamber and arranged to irradiate a sample volume of the material with a plurality of wavelengths of light, a wavelength separator disposed in the second chamber, the wavelength separator receiving light reflected from the irradiated sample volume to produce spatially separated light of different wavelengths, and a detector disposed in the second chamber and positioned to receive the spatially separated light from the wavelength separator, the detector transmitting a signal representative of the intensity of the spatially separated light received from the wavelength separator; wherein the first and second window are in substantially the same plane.

9. The probe head of claim 8, wherein the light source irradiates light through the first window onto a sample volume.

10. The probe head of claim 9, wherein the wavelength separator receives light through the second window from the irradiated sample volume.

11. The probe head of claim 8, wherein the detector in the second chamber is hermetically sealed.

12. The probe head of claim 11, further comprising a reflector positioned in the housing to reflect a portion of light emanating from the light source into the second chamber for calibration measurements.

13. The probe head of claim 8, further comprising a reference shutter for selectively blocking light emitted from the irradiated sample volume from reaching the detector to facilitate calibration of the spectrometer.

14. The probe head of claim 8, wherein the light source irradiates the sample volume with light in a visible to mid infrared spectral region.

15. The probe head of claim 8, further comprising a diffuser for diffusing light reflected from the irradiated sample volume into the wavelength separator.

16. The probe head of claim 8, wherein color components of the sample volume are determined based on intensities of the wavelengths of the spatially separated light received by the detector.

17. The probe head of claim 8, wherein the detector has a viewing aperture greater than about 0.5 square inches.

18. The probe head of claim 8, wherein the detector has a viewing aperture between about 0.5 square inches and about 10 square inches.

19. The probe head of claim 8, wherein the light source illuminates a spot size greater than about 0.5 square inches.

20. The probe head of claim 8, wherein the light source illuminates a spot size between about 0.5 square inches and about 10 square inches.

21. The probe head of claim 8, further comprising an optical blocking element positioned in an optical path between the light source and the detector to force the optical path into the sample volume.

22. A spectrometer for analyzing a material, the spectrometer comprising:
   a probe head comprising
      a housing having a first chamber, which includes a solid transparent first window separated from a second chamber, which includes a solid transparent second window,
      a light source disposed in the first chamber arranged to irradiate a sample volume of the material with a plurality of wavelengths of light,
      a wavelength separator disposed in the second chamber, the wavelength separator receiving light reflected from the irradiated sample volume to produce spatially separated light of different wavelengths, and
      a detector disposed in the second chamber and positioned to receive the spatially separated light from the wavelength separator, the detector generating a signal representative of the intensity of the spatially separated light received from the wavelength separator, and
   a computer coupled to the detector and housed separately from the probe head, the computer receiving the signal generated by the detector and analyzing the sample volume based on the signal; wherein the first window and second window are in substantially the same plane.

23. The spectrometer of claim 22, further comprising an analog to digital converter coupled to the detector and the computer, the analog to digital converter converting the signal from the detector from an analog signal to a digital signal for receipt by the computer.

24. The spectrometer of claim 22, wherein the housing of the probe head is so positioned that the first window is disposed in a sample containment apparatus.

25. A method of spectroscopically analyzing a material with a spectrometer, the method comprising:
   irradiating a sample volume of the material with a plurality of wavelengths of light from a light source positioned in a first chamber,
   receiving light reflected from the irradiated sample volume in a second chamber,
   so positioning an optical blocking element as thereby to inhibit reception of light that has been reflected from the sample's surface, and
   separating wavelengths of the received light to produce spatially separated light of different wavelengths, and
   detecting intensity of the spatially separated light with a detector positioned in the second chamber and connected to the spectrometer.

26. The method of claim 25, further comprising the step of selectively reflecting a portion of light emanating from the light source into the second chamber for calibration measurements.

27. The method of claim 25, wherein light from the light source is within a visible to mid infrared spectral region.

28. The method of claim 25, further comprising the step of diffusing light reflected from the irradiated sample volume.

29. The method of claim 25, further comprising the step of determining constituent components of the sample volume based on the detected intensity.

30. The method of claim 25, further comprising the step of determining color components of the sample volume based on the detected intensity.

31. The method of claim 25, wherein the light source illuminates a spot size greater than about 0.5 square inches.

32. The method of claim 25, wherein the light source illuminates a spot size between about 0.5 square inches and about 10 square inches.

33. The method of claim 25, wherein the detector has a viewing aperture greater than about 0.5 square inches.

34. The method of claim 25, wherein the detector has a viewing aperture between about 0.5 square inches and about 10 square inches.

35. The method of claim 25, further comprising the step of forcing an optical path between the light source and the detector into the sample volume.

36. A method of spectroscopically analyzing a material flowing within a sample containment apparatus, the method comprising:
   positioning a probe head of a spectrometer on the sample containment apparatus.
   irradiating a sample volume of the material within the sample containment apparatus with a plurality of wavelengths of light from a light source positioned in a first chamber of the probe head,
   receiving light reflected from the irradiated sample volume in a second chamber of the probe head,
   separating wavelengths of the received light to produce spatially separated light of different wavelengths, and
   detecting intensity of the spatially separated light with a detector positioned in the second chamber.

* * * * *